United States Patent [19]

Drake et al.

[11] 4,255,352

[45] Mar. 10, 1981

[54] PREPARATION OF UNSATURATED NITRILES

[75] Inventors: Charles A. Drake; Stanley J. Marwil, both of Bartlesville, Okla.

[73] Assignee: Phillips Petroleum Company, Bartlesville, Okla.

[21] Appl. No.: 32,974

[22] Filed: Apr. 24, 1979

[51] Int. Cl.[2] .................. C07C 120/00; C07C 121/46; C07C 121/20; C07C 121/66

[52] U.S. Cl. ............................. 260/465.8 R; 260/464; 260/465 H; 260/465 K; 260/465.9

[58] Field of Search ............ 260/464, 465.8 R, 465.9, 260/465 K, 465 H

[56] References Cited

U.S. PATENT DOCUMENTS

| | | | |
|---|---|---|---|
| 2,641,607 | 6/1953 | Albisetti, Jr. et al. | 260/465.3 |
| 3,296,108 | 1/1967 | Hutson, Jr. et al. | 204/163 |
| 3,652,642 | 3/1972 | Baba | 260/464 X |
| 3,840,583 | 10/1974 | Turk et al. | 260/465.8 R |
| 3,883,606 | 5/1975 | Banks | 260/465.9 X |
| 3,985,786 | 10/1976 | Drake | 260/465.8 R |

OTHER PUBLICATIONS

MacDonald, et al., Chem. Eng. Progress, 47, pp. 363–369, 1951.

Albisetti, et al., J.A.C.S., 78, (1956), pp. 2637–2641.

Chemical Engineers Handbook, 5th Ed., (1973) pp. 4–20 to 4–22.

*Primary Examiner*—Joseph Paul Brust

[57] ABSTRACT

An olefinically unsaturated nitrile, an olefinic hydrocarbon containing an allylic hydrogen and a monoadduct reaction product of an olefinic hydrocarbon and an olefinically unsaturated nitrile are contacted in a plurality of tank reactors in series in the presence of a diluent to produce unsaturated dinitriles.

24 Claims, No Drawings

PREPARATION OF UNSATURATED NITRILES

This invention relates to the production of unsaturated dinitriles. In a specific aspect this invention relates to a reaction of an olefinically unsaturated nitrile, an olefinic hydrocarbon and a monoadduct of an olefinic hydrocarbon and an olefinically unsaturated nitrile in a plurality of reactors in series in the presence of a diluent to yield olefinically unsaturated dinitrile products having a greater number of carbon atoms than the unsaturated nitrile reactant.

In U.S. Pat. No. 2,641,607 (issued June 9, 1953), Albisetti et al describe the thermal reaction of a 2-alkenenitrile (e.g. acrylonitrile) with a neutral olefinic compound (e.g. isobutylene) in a first stage reaction to produce unsaturated mononitriles having a greater number of carbon atoms (e.g. 5methyl-5-hexenenitrile). Albisetti et al state that the reaction effluent can be distilled to recover the unsaturated mononitrile product, and that the recovered unsaturated mononitrile product can be thermally reacted with a neutral olefinic compound in a second stage reaction to produce unsaturated dinitriles. The patentees state that the first stage reaction can be conducted in the presence or absence of an inert diluent or solvent. The patent lists hydrocarbons, ethers and esters as suitable inert organic solvents, and then states that the reaction also takes place in the presence of water as a diluent, the water serving as a heat transfer medium.

In J. Am. Chem. Soc. 78, pp. 2637–2641 (1956), Albisetti et al describe further work with the thermal reaction of a 2-alkenenitrile with a neutral olefinic compound in a first stage and the subsequent reaction in a second stage of a neutral olefinic compound with the reaction product of the first stage to produce unsaturated dinitriles. The authors state that water can be employed as the reaction medium in the second stage reaction of acrylonitrile with 5-methyl-5-hexenenitrile to produce 5-methylenenonanedinitrile. The authors also state that in the case of polymerizable nitriles, the use of water as the medium prevented formation of tars.

In U.S. Pat. No. 3,840,583 (issued Oct. 8, 1974) Turk et al disclose that the yield of unsaturated dinitriles can be increased by contacting an unsaturated mononitrile, an olefin and a monoadduct reaction product of an unsaturated mononitrile and an olefin wherein the monoadduct reaction product is present in significant amount during substantially the entire reaction period. The patentees stated that this single stage reaction could be carried out in the presence or absence of a solvent or diluent which is nonreactive with either the reactants or the reaction products. The patentees list various hydrocarbons, various ethers, tetrahydrofuran, dioxane, carbon tetrachloride and methylene chloride as representative commercially available nonreactive solvets that can be employed.

In U.S. Pat. No. 3,985,786 (issued Oct. 12, 1976) Drake discloses that the utilization of an aqueous medium as the diluent in the Turk et al single stage process provides a greater increase in the yield of unsaturated dinitriles than would be expected from the summation of the increase in yield in unsaturated dinitriles achieved by the utilization of water as the diluent in both stages of the Albisetti et al process and the increase in yield in unsaturated dinitriles achieved by the utilization of the Turk et al single stage reaction instead of the Albisetti et al two stage process.

In the past, the reactions described in the referenced patents and publication appear to have been carried out in a single conventional agitated tank-type reactor. It has now been discovered that the use of a plurality of tank-type reactors in series in the Turk et al and Drake single stage process provides an increased percentage conversion of the reactants and a decreased production of undesired heavy products where the total residence time in the one large conventional agitated tank type reactor is the same as the total residence time in the plurality of smaller tank type reactors.

In the past, the reactions described in the referenced patents and publications have been carried out by introducing the feed into an upper zone of the tank-type reactor and withdrawing the products from a lower zone of the tank-type reactor (downflow operation). It has now been found that, for a plurality of tank type reactors in series, introducing the feed into a lower zone of each of the reactors and removing the product from an upper zone of each of the reactors (upflow operation) provides an increased percentage conversion of reactants, a decreased production of undesired heavy products and an increase in reactor productivity.

Accordingly, it is an object of this invention to provide an improved process for the reaction of an olefinic hydrocarbon and an olefinically unsaturated nitrile in order to obtain an olefinically unsaturated dinitrile reaction product having a greater number of carbon atoms than the original nitrile. Another object is to provide an improved process which results in increased yields of high carbon number olefinically unsaturated dinitrile reaction products. Another object of the invention is to increase the percentage conversion of the reactants. Yet another object of the invention is to decrease the production of undesired heavy byproducts. Other objects, aspects and advantages of the invention will be apparent from a study of the specification and the appended claims to the invention.

Any unsaturated mononitrile can be employed in the practice of this invention provided the mononitrile contains ethylenic unsaturation, contains at least one hydrogen atom attached to a doubly bonded carbon atom, and contains a cyano group attached to a carbon atom adjacent and doubly bonded to a carbon atom which is attached to at least one hydrogen atom. Preferably the mononitrile reactant is free of acetylenic unsaturation and contains from 1 to 2 ethylenically unsaturated, nonconjugated double bonds as the sole aliphatic unsaturation, while the total number of carbon atoms in the mononitrile reactant is within the range of 3 to 18, more preferably within the range of 3 to 8. Illustrative unsaturated mononitrile reactants include those represented by the formula

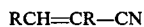

RCH=CR—CN wherein each R is independently selected from the group consisting of hydrogen and hydrocarbyl radicals. Preferably the hydrocarbyl radicals are selected from the group consisting of alkyl, cycloalkyl, and aryl hydrocarbyl radicals and combinations thereof, such as alkylcycloalkyl, cycloalkylalkyl, aralkyl and arylcycloalkyl radicals. Examples of unsaturated nitriles meeting the requirement, of the above formula are acrylonitrile, methacrylonitrile, 2-decenenitrile, 3-cyclohexyl-2 propenenitrile, 4-phenyl-2-butenenitrile, 3(p-tolyl)-2-propenenitrile, 2-butenenitrile, 2-hexenenitrile, 5-methyl-2-hexenenitrile, 4-methyl-2-heptenenitrile, 6,6,8,8- tetramethyl-2-nonenenitrile, 6-cyclohexyl-2-octenenitrile, 6-phenyl-2-decenenitrile, 2-octadecenenitrile, 6,7,8-trimethyl-9-phenyl-2-nonenenitrile, 5-p-tolyl-2-nonenenitrile, and the like, and mixtures of any two or more thereof.

Any acyclic or cyclic olefinic hydrocarbon compound can be employed in the practice of this invention, provided that the compound has at least one olefinic linkage having joined to one of the doubly bonded carbons a carbon atom having at least one hydrogen atom attached thereto, said doubly bonded carbon atoms being free of cyano groups attached thereto. The olefinic hydrocarbons preferably are free of acetylenic unsaturation and have from 3 to 18 carbon atoms per molecule with from 1 to 2 ethylenically unsaturated, nonconjugated double bonds as the sole aliphatic unsaturation. The preferred types of these compounds are the open chain monoolefinic hydrocarbons represented by the formula $$R'_2C{=}CR'{-}CHR'_2$$

wherein each R' is independently selected from the group consisting of hydrogen and hydrocarbyl radicals. The hydrocarbyl radicals are preferably selected from the group consisting of alkyl, cycloalkyl, and aryl hydrocarbyl radicals and combinations thereof. Especially preferred are those monoolefinic hydrocarbons having 3 to 12 carbon atoms and having an alkyl group, preferably methyl, as a side chain attached to at least one of the carbon atoms comprising the ethylenic linkage. Specific examples of olefinically unsaturated hydrocarbon compounds which are useful in the process of this invention include propylene, isobutylene, diisobutylene, triisobutylene, 1,5-hexadiene, beta-pinene, 1,5-cyclooctadiene, 2,4,4-trimethyl-1-pentene, 2-butene, biallyl, bimethallyl, alpha-methylstyrene, beta-methylstyrene, 1-pentene, 1-decene, cyclohexene, 1-allylcyclohexene, 3-allycyclohexene, 4-allylcyclohexene, allylbenzene, 3,4,4-trimethyl-2-pentene, 1-dodecene, 2,3- dimethyl-2-butene, and 2-methyl-1-phenyl-2-propene, and the like, and mixtures of any two or more thereof.

Suitable monoadduct reactants include any monoadduct reaction product of an olefinic hydrocarbon, as hereinabove defined, and an unsaturated mononitrile, as hereinabove defined. It is believed that the olefinic hydrocarbon compound and the unsaturated mononitrile react in accordance with the "ene" reaction to produce, as the principal monoadduct reaction product, a compound having the structural formula

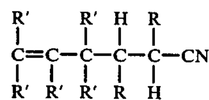

Generally, a lesser amount of an isomeric monoadduct reaction product having the formula

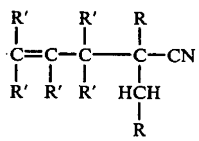

is also produced. Thus, isobutylene and acrylonitrile react to produce 5-methyl-5-hexenenitrile as the principal monoadduct reaction product along with a small amount of 2,4-dimethyl-4-pentenenitrile. It can be readily seen that isobutylene as the olefinic hydrocarbon reactant possesses six of the required allylic hydrogens but that all six are structurally equivalent so that only two monoadduct reaction compounds corresponding to the above general formulas are produced according to the "ene" reaction.

However, it will also be evident that if a compound having two or more allylic hydrogens which are not structurally equivalent is employed as the olefinic hydrocarbon reactant, the number of expected isomeric monoadduct reaction product compounds having the above general formulas will be increased. For example, if 2,4,4-trimethyl-1-pentene is reacted with acrylonitrile the major monoadduct reaction products expected according to the "ene" reaction would be 5-methylene-7,7-dimethyloctanenitrile and 4-methylene-2,6,6-trimethylhepatanenitrile with lesser amounts of 5,7,7-trimethyl-5-octenenitrile and 4-t-butyl-5-methyl-5-hexenenitrile. Other factors, not fully understood at present, may influence the relative amounts of the possible isomers in the monoadduct reaction product and in other instances presently employed analytical methods may not distinguish the various isomers present. Indeed, the monoadduct reaction product finds utility in many applications with no need of a costly separation of the isomers present in the monoadduct reaction product. The isomeric mixture reaction product produced by the reaction of an olefinic hydrocarbon and an olefinically unsaturated nitrile can be employed as the monoadduct reactant, or one or more isomers can be separated from the isomeric mixture reaction product and such separated isomer or isomers can be employed as the monoadduct reactant. Examples of suitable monoadduct reactants include 5-methyl-5-hexenenitrile, 3,5-dimethyl-5-hexenenitrile, 3-(n-propyl)-5-hexenenitrile, 3-(n-propyl)-6-phenyl-5-hexenenitrile, 2,4-dimethyl-4-pentenenitrile, 2-ethyl-4-methyl-4-pentenenitrile, 2(n-butyl)-4-pentenenitrile, 2-(n-butyl)-5-phenyl-4-pentenenitrile, and mixtures of any two or more thereof.

The diadduct reaction products obtained by the process of this invention comprise the reaction product mixtures formed by the monoaddition of an unsaturated mononitrile and any monoadduct reaction product. Exemplary of a diadduct reaction product is the reaction product mixture, comprising the major isomer species 5-methylenenonanedinitrile and 5-methyl-4-nonenedinitrile, that contains minor isomer species 2-methyl-4-methyleneoctanedinitrile, 2,4-dimethyl-4-octenedinitrile, 2,4-dimethyl-3-octenedinitrile, 2,6-dimethyl-4-methyleneheptanedinitrile and 2,4,6-trimethyl-3-heptenedinitrile.

Any amount of olefinic hydrocarbon, olefinically unsaturated mononitrile and monoadduct reaction product can be employed in the practice of this invention. In general, the mol ratio of olefinically unsaturated mononitrile reactant to olefinic hydrocarbon reactant will be in the range of about 10:1 to about 0.1:1, preferably in the range of about 2:1 to about 0.3:1. In general, the monoadduct reaction product will be employed in an amount such that, during substantially the entire reaction period, the net monoadduct reaction product present in the reaction mixture wil constitute from about 10 to about 90, preferably from about 20 to about 80, and more preferably from about 30 to about 70 weight percent of the total reaction mixture. The net amount of monoadduct reaction product present in the reaction zone is the sum of the amount of monoadduct reaction product charged to the reaction zone plus the amount of monoadduct reaction product produced by the reaction of the olefinic hydrocarbon reactant and the olefinically unsaturated mononitrile reactant in the reaction zone less the monoadduct reaction product consumed by reaction with the olefinically unsaturated mononitrile in the reaction zone to produce diadduct. The monoadduct reaction product charged to the reaction zone can be the same as or different from the monoadduct reaction product produced by the reaction of the olefinic hydrocarbon reactant and the olefinically unsaturated mononitrile reactant in the reaction zone, but it will be generally preferred for them to be the same. The total reaction mixture includes all fluid materials present in the reaction zone, i.e. reactants, diluents, products, byproducts, etc.

Any suitable tank reactor can be employed in the practice of the invention. The tank reactor is preferably equipped with some means for agitating the reactants in the tank. Any suitable number (at least two) of tank reactors in series can be employed in the practice of the invention. Three tank reactors in series are presently preferred.

Any suitable reaction conditions for a continuous process can be employed in the practice of the invention. The reaction time employed in the practice of this invention can vary widely. The liquid hourly space velocity will generally be in the range of about 0.05 to about 20, preferably in the range of about 0.1 to about 10, more preferably in the range of about 0.5 to about 2.

The reaction temperatures that can be employed in the practice of the invention can vary widely. Generally, however, suitable reaction temperatures are within the range of from about 100° C. to about 500° C., and preferred reaction temperatures are within the range of from about 200° C. to about 350° C.

The reaction pressures suited to the practice of this invention also vary widely. Reaction pressures within a range of from about atmospheric pressure to about 100,000 psig (690 MPa) can be employed; however, reaction pressures within the range of from about 500 psig (3.5 MPa) to about 4000 psig (27.5 MPa) are preferably employed.

If desired, the processes of this invention can be carried out in the presence of a polymerization inhibitor. The use of the inhibitor often advantageously limits side reactions such as the dimerization or polymerization of the olefinically unsaturated mononitrile. When an inhibitor is employed, it is generally desirable that an ampunt of from about 0.001 to about 5, preferably from about 0.1 to about 1, percent by weight inhibitor based on the weight of unsaturated mononitrile reactant be employed. Suitable inhibitors include hydroquinone, 2,6-di-tert-butyl-para-cresol, 2,6-di-tert-butylhydroquinone, 4-tert-butylcatechol, para-hydroxydiphenylamine, and the like, and mixtures of any two or more thereof.

The reaction of the above described olefinic hydrocarbon reactant, olefinically unsaturated mononitrile reactant and monoadduct reaction product reactant is carried out in the presence of any suitable diluent. Preferably the diluent comprises at least 50 weight percent water, more preferably at least 80 weight percent water, and more preferably consists essentially of water. The codiluent with water, if employed, can be any solvent or diluent which is nonreactive with either the reactants or the reaction products. Examples of suitable codiluents include benzene, toluene, para-xylene, ortho-xylene, meta-xylene, ethylbenzene, diethyl ether, ethyl propyl ether, dibutyl ether, tetrahydrofuran, dioxane, cyclohexane, carbon tetrachloride, methylene chloride, and the like, and mixtures of any two or more thereof.

The diluent can be employed in any suitable amount where upflow operation is being utilized. In general, the diluent will be employed in an amount in the range of about 0.01 to about 40 parts by weight of total diluent per part by weight of olefinically unsaturated mononitrile reactant charged to the reaction zone. The amount of diluent currently preferred is in the range of about 0.1 to about 20 parts by weight of total diluent per part by weight of olefinically unsaturated mononitrile reactant charged to the reaction zone. The advantages of the preferred aqueous diluent system include improved selectivity to the desired olefinically unsaturated nitrile and reduced amounts of heavy polymeric byproduct. This latter byproduct is particularly objectionable because it tends to foul reactor surfaces.

The amount of diluent employed is critical where downflow operation is being utilized. In general, the diluent employed will be in the range of about 0.01 to about 1.25 parts by weight of total diluent per part by weight of olefinically unsaturated mononitrile reactant charged to the reaction zone. The amount of diluent currently preferred for downflow operation is in the range of about 0.05 to about 1 parts by weight of total diluent per part by weight of olefinically unsaturated mononitrile reactant charged to the reaction zone.

A convenient method of carrying out this invention comprises combining a mixture of an olefinically unsaturated mononitrile (e.g. acrylonitrile), an olefinic hydrocarbon compound (e.g. isobutylene), and a monoadduct reaction product reactant (e.g. a mixture of 5-methyl-5-hexenenitrile and 2,4-dimethyl-4-pentenenitrile) with a diluent fluid (water) and then continuously introducing the combined mixture of reactants and diluent fluid into the first one of a plurality of heated tank reactors in series. The temperature of each of the plurality of tank reactors is maintained within the range of about 200° to about 250° C.; the pressure in each of the plurality of tank reactors is maintained from about 500 to about 4000 psig; the mol ratio of the olefinically unsaturated mononitrile to the olefinic hydrocarbon is maintained in the range of about 5:1 to about 0.2:1; the concentration of the monoadduct reaction product in the reaction mixture is maintained in the range of about 20 to about 80 weight percent; and the liquid hourly space velocity is maintained in the range of about 0.5 to about 2. The resulting olefinically unsaturated dinitrile reaction product, which is removed as the product from the last one of the plurality of tank reactors in series, is readily isolated from the reaction effluent mixture by any convenient product recovery method such as fractional distillation.

As has been previously stated, the use of a plurality of tank reactors in series in contrast to a single tank reactor results in an improved process. Also, upflow operation of the plurality of tank reactors in series in contrast to downflow operation results in an improved process. It is thus preferred to operate the plurality of tank reactors in series by introducing the feed into a lower zone of the first tank reactor and removing the product from an upper zone of the first tank reactor. The thus removed product from the first reactor is then introduced into a lower zone of the second tank reactor in the series and this process is continued until the product is removed from an upper zone in the last one of the plurality of tank reactors in series.

If desired, the reaction can be carried out in the presence of any suitable promoter, for example an organo derivative of a Group VA element defined by the following formula $R'''_nZH_{3-n}$ wherein each R''' is independently selected from the group consisting of aryl, alkaryl, cycloalkylaryl, ararylaryloxy, alkaryloxy, arylaryloxy; wherein each R''' group contains from 6 to 12 carbon atoms; Z is selected from the group consisting of N,P,P=O, As, Sb, or Bi; and n is 2 or 3. Illustrative of organo derivatives of the Group VA elements defined by the above formula are the following compounds: triphenylphosphine, diphenylphosphine, tris(hexylphenyl)phosphine, tris(cyclohexylphenyl)phosphine, dinaphthylphosphine, tris(4-biphenyl)phosphine, tris(4-butylphenyl)phosphine, triphenylamine, diphenylamine, tris (3,5-dipropylphenyl)amine, triphenylarsine, tris(pentylphenyl)arsine, triphenylbismuthine, diphenylarsine, diphenyl-4-biphenylphosphine, tris(p-tolyl)stibine, tris(3,5-dimethylphenyl)bismuthine, diphenyl(4-ethylphenyl)phosphine, diphenoxy(phenyl)phosphine, diphenyl(p-methylphenoxy)phosphine, triphenylphosphite, diphenyl(p-tolyl)phosphine, triphenylphosphate, and the like, and mixtures of any two or more thereof. The variant designated by n in mixtures of promoters represented by the formula $R'''_nZH_{3-n}$ can vary, with the arithmetical sum of the value of n of individual promoters, from 2 to 3. The term "reaction promoting material" includes materials commonly called catalysts as well as materials commonly called promoters.

If employed, the amount of promoter utilized in the process of this invention can vary widely. In general, the mol ratio of promoter to unsaturated mononitrile reactant charged to the reaction zone would be in the range of about 1:20 to about 1:1. Preferably, the mol ratio of promoter to unsaturated mononitrile reactant charge would be in the range of about 1:10 to about 1:3.

The following examples are presented in further illustration of the invention but should not be unduly construed in limitation thereof.

EXAMPLE I

The following runs were conducted to illustrate the advantages of utilizing a plurality of tank reactors in series in contrast to utilizing a single tank reactor. The following runs were conducted using either a 1 liter autoclave reactor or three 300 cc autoclave reactors in series. All runs were conducted at a reaction temperature of 280° C., pressure of 2500 psig (17 MPa) and reactor residence time of 0.6 hour. The approximate composition (weight percent) of the organic feed was:

| | |
|---|---|
| Acrylonitrile (ACN) | 13.3 weight percent |
| Isobutylene | 24.2 weight percent |
| Monoadduct (MA) mixture of approximately 95 percent 5-methyl-5-hexenenitrile with approximately 5 weight percent 2,4-dimethyl-4-pentenenitrile | 62.5 weight percent |

Sufficient water was added to maintain a desired water/acrylonitrile weight ratio. The isobutylene/monoadduct weight ratio was 0.75. The total olefin to acrylonitrile mole ratio was 4:1.

When steady state conditions had been established, typically after about 5 hours run time, a product sample was obtained by known methods and analyzed by fractional distillation and gas-liquid chromatographic analysis of the resulting fraction.

The monoadduct was added in the reactor feed to simulate recycle of that material. The yield of monoadduct was obtained by subtracting the monoadduct fed into the reactors from the monoadduct in the effluent flowing from the ractors. It was desired that there be no net change in the monoadduct composition during the reaction but, as Table I illustrates, this condition was only approached. The organic raw materials and water were fed at a rate to give a calculated residence time in the reactor of 0.6 hour for both the single reactor and the three reactors in series. For instance, for runs 1,3 and 5 the measured flow rates at room temperature was 19.8 cc/minutes for the organic feed and 0.41 cc/minute for the water. These flow rates, when corrected for the thermal expansion of the liquids from room temperature to reaction temperature, gave the desired residence time. For runs 2, 4 and 6, because of the slightly reduced reactor volume, the flow rates were adjusted to 17.8 cc/minute and 0.37 cc/minute for the organic phase and water phase, respectively, to provide a residence time in the three reactors in series of 0.6 hour. All runs were made under down flow operation.

TABLE I

Effect of Reactor Type on Diadduct Production

| Run No. | Reactor* Type | $H_2O$:ACN Weight Ratio | ACN Conv. % | Yield Based on ACN Converted, % MA | Byproduct | DA | MA + DA | Heavies |
|---|---|---|---|---|---|---|---|---|
| 1 | 1 | 0.25 | 52.4 | −4.2 | 3.0 | 83.0 | 78.8 | 18.2 |
| 2 | 3 | 0.25 | 54.8 | 1.1 | 3.5 | 79.6 | 80.7 | 15.8 |
| 3 | 1 | 0.5 | 51.3 | −3.5 | 3.4 | 85.6 | 82.1 | 14.5 |
| 4 | 3 | 0.5 | 53 | 1.9 | 3.8 | 79.3 | 81.2 | 15.0 |
| 5 | 1 | 1.3 | 48.7 | −4.4 | 4.4 | 88.5 | 84.1 | 11.5 |
| 6 | 3 | 1.3 | 48.6 | 0.5 | 4.3 | 83.8 | 84.3 | 11.4 |

*1 = a single reactor, 3 = 3 reactors in series.

A comparison of run 1 with run 2 shows a significant decrease in the production of undesirable heavy products and a significant increase in the percentage conversion of the acrylonitrile. A comparison of run 3 with run 4 also shows a significant increase in the percentage conversion of acrylonitrile but does not show a decrease in the production of undesirable heavy products. A comparison of run 5 with run 6 does not show a significant decrease in the production of undesirable heavy products or a significant change in the conversion of the acrylonitrile. It thus appears that the lower weight ratios of water to acrylonitrile are desirable and are in fact required to provide the improved process operation advantages of three reactors in series where downflow operation is utilized.

EXAMPLE II

Utilizing the reaction conditions set forth in Example I and the three 300 cc reactors in series, comparative data was taken for both down flow and up flow operation of the three 300 cc reactors in series. This data is presented in Table II.

TABLE II

Effect of Reactor Operation on Diadduct Production

| Run No. | Operation U (Upflow) D (Downflow) | Temp, °C. | $H_2O$:ACN Weight Ratio | ACN Conv. % | Yield Based on ACN Converted, % MA | Byproduct | DA | MA + DA | Heavies |
|---|---|---|---|---|---|---|---|---|---|
| 1 | D | 270 | 0.25 | 48 | 1.8 | 4.2 | 78.5 | 80.3 | 15.5 |
| 2 | U | 270 | 0.25 | 49 | 2.2 | 3.7 | 79.9 | 82.1 | 14.2 |
| 3 | D | 280 | 0.5 | 53 | 1.9 | 3.9 | 79.4 | 81.3 | 14.8 |
| 4 | U | 280 | 0.5 | 56 | 1.2 | 3.7 | 81.7 | 82.9 | 13.4 |
| 5 | D | 280 | 1.3 | 48.6 | 0.5 | 4.3 | 83.8 | 84.3 | 11.4 |
| 6 | U | 280 | 1.3 | 53.5 | 4.7 | 4.0 | 81.1 | 85.8 | 10.2 |

A comparison of the up flow and down flow operations set forth in Table II illustrates that there was a significant decrease in the production of undesirable heavy products obtained by operating the three reactors in series in an up flow manner rather than a down flow manner. It is further noted that there was an increased percent conversion of acrylonitrile for up flow operation and an increased reactor productivity for upflow operation.

Reasonable variations and modifications are possible within the scope of the foregoing disclosure and the appended claims to the invention.

That which is claimed is:

1. A process which comprises contacting at least one olefinic hydrocarbon reactant, at least one olefinically unsaturated mononitrile reactant and at least one monoadduct reaction product of an olefinic hydrocarbon compound and an olefinically unsaturated mononitrile compound, in a plurality of tank reactors in series in the presence of a diluent, under reaction conditions suitable to produce at least one olefinically unsaturated dinitrile product, each of said olefinically unsaturated mononitrile reactant and said olefinically unsaturated mononitrile compound containing at least one hydrogen atom attached to a doubly bonded carbon atom and containing a cyano group attached to a carbon atom adjacent and doubly bonded to a carbon atom which is attached to at least one hydrogen atom, each of said olefinic hydrocarbon reactant and said olefinic hydrocarbon compound having at least one olefinic linkage having joined to one of the doubly bonded carbons a carbon atom having at least one hydorgen atom attached thereto, wherein at substantially any point in said plurality of tank reactors in series the concentration of said monoadduct reaction product in the resulting reaction mixture is within the range of about 10 to about 90 weight percent of the total reaction mixture, wherein the amount of said diluent is in the range of about 0.01 to about 1.25 parts by weight of total diluent per part by weight of said olefinically unsaturated mononitrile reactant if at least one of said plurality of tank reactors in series is operated downflow, and wherein the amount of said diluent is in the range of about 0.01 to about 40 parts by weight of total diluent per part by weight of said olefinically unsaturated mononitrile reactant if all of said plurality of tank reactors in series are operated upflow.

2. A process in accordance with claim 1 wherein said plurality of tank reactors in series comprises three tank reactors in series.

3. A process in accordance with claim 2 wherein each of said plurality of tank reactors is a stirred tank reactor.

4. A process in accordance with claim 1 wherein said at least one olefinic hydrocarbon reactant, said at least one olefinically unsaturated mononitrile reactant, said at least one monoadduct reaction product of an olefinic hydrocarbon compound and an olefinically unsaturated mononitrile compound, and said diluent are introduced into a lower zone of a first one of said plurality of tank reactors in series; any unreacted reactants and the reaction products from said first one of said plurality of tank reactors in series being removed from an upper zone of said first one of said plurality of tank reactors in series and being introduced into a lower zone of the second tank reactor in the series; the process of introducing reactants and reaction products into a lower zone of each tank reactor in series and removing reactants and reaction products from an upper zone of each tank reactor in series continuing until said at least one olefinically unsaturated dinitrile product is removed from an upper zone of the last tank reactor in the series.

5. A process in accordance with claim 1 wherein each of said at least one olefinic hydrocarbon reactant and said olefinic hydrocarbon compound is free of acetylenic unsaturation and has from 3 to 18 carbon atoms per molecule with from 1 to 2 ethylenically unsaturated, nonconjugated double bonds as the sole aliphatic unsaturation.

6. A process in accordance with claim 5 wherein each of said at least one olefinically unsaturated mononitrile reactant and said olefinically unsaturated mononitrile compound is free of acetylenic unsaturation, has from 1 to 2 ethylenically unsaturated, nonconjugated double bonds as the sole aliphatic unsaturation, and has from 3 to 18 carbon atoms per molecule.

7. A process in accordance with claim 6 wherein each of said at least one olefinic hydrocarbon reactant and said olefinic hydrocarbon compound is represented by the formula $R'_2C{=}CR'{-}CHR'_2$, wherein each R' is independently selected from the group consisting of hydrogen and hydrocarbyl radicals; and wherein each of said at least one olefinically unsaturated mononitrile reactant and said olefinically unsaturated mononitrile compound is represented by the formula $RCH{=}CR{-}CN$ wherein each R is independently selected from the group consisting of hydrogen and hydrocarbyl radicals.

8. A process in accordance with claim 7 wherein said reaction conditions comprise a temperature in the range of about 240° C. to about 350° C., a pressure in the range of about 1000 to about 4000 psig, a contact time in the range of about 30 minutes to about 10 hours, and a mole ratio of said olefinically unsaturated mononitrile reactant to said olefinic hydrocarbon reactant in the range of about 5:1 to about 0.2:1; and wherein said at least one monoadduct reaction product comprises compounds having the structural formula

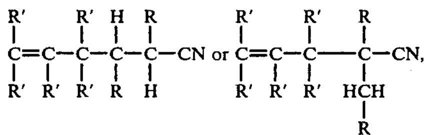

wherein R and R' are as defined above; and further comprising recovering from the resulting reaction effluent said at least one olefinically unsaturated dinitrile reaction product.

9. A process in accordance with claim 7 wherein said reaction conditions comprise a temperature in the range of about 100° C. to about 500° C., a pressure in the range of about atmospheric to about 100,000 psig, and a mole ratio of said olefinically unsaturated mononitrile reactant to said olefinic hydrocarbon reactant in the range of about 10:1 to about 0.1:1.

10. A process in accordance with claim 9 wherein said diluent comprises at least 50 weight percent water; the balance, if any, of said diluent being nonreactive with the reactants and the reactant products.

11. A process in accordance with claim 10 wherein at substantially any point in said plurality of tank reactors in series, said concentration of monoadduct reaction product in said reaction mixture is maintained within the range of about 20 to about 80 weight percent.

12. A process in accordance with claim 11 wherein said at least one olefinically unsaturated mononitrile reactant is acrylonitrile, wherein said olefinically unsaturated mononitrile compound is acrylonitrile, wherein said at least one olefinic hydrocarbon reactant is isobutylene, and wherein said olefinic hydrocarbon compound is isobutylene.

13. A process in accordance with claim 1 wherein said reaction conditions comprise a temperature in the range of about 100° C. to about 500° C., a pressure in the range of about atmospheric to about 100,000 psig, and a mole ratio of said olefinically unsaturated mononitrile reactant to said olefinic hydrocarbon reactant in the range of about 10:1 to about 0.1:1.

14. A process in accordance with claim 13 wherein said at least one olefinically unsaturated mononitrile reactant is acrylonitrile, wherein said olefinically unsaturated mononitrile compound is acrylonitrile, wherein said at least one olefinic hydrocarbon reactant is isobutylene, and wherein said olefinic hydrocarbon compound is isobutylene.

15. A process in accordance with claim 1 wherein each of said at least one olefinic hydrocarbon reactant and said olefinic hydrocarbon compound has from 3 to 18 carbon atoms and is represented by the formula $R'_2C{=}CR'{-}CHR'_2$, wherein each R' is independently selected from the group consisting of hydrogen and hydrocarbyl radials; and wherein each of said at least one olefinically unsaturated mononitrile reactant and said olefinically unsaturated mononitrile compound has from 3 to 18 carbon atoms and is represented by the formula $RCH{=}CR{-}CN$ wherein each R is independently selected from the group consisting of hydrogen and hydrocarbyl radicals.

16. A process in accordance with claim 15 wherein said reaction conditions comprise a temperature in the range of about 100° C. to about 500° C., a pressure in the range of about atmospheric to about 100,000 psig, and a mole ratio of said olefinically unsaturated mononitrile reactant to said olefinic hydrocarbon reactant in the range of about 10:1 to about 0.1:1, and wherein said diluent comprises at least 50 weight percent water; the balance; if any, of said diluent being nonreactive with the reactants and the reaction products.

17. A process which comprises contacting at least one olefinic hydrocarbon reactant, at least one olefinically unsaturated mononitrile reactant and at least one monoadduct reaction product of an olefinic hydrocarbon compound and an olefinically unsaturated mononitrile compound, a plurality of tank reactors in series in the presence of a diluent, under reaction conditions suitable to produce at least one olefinically unsaturated dinitrile product;

wherein each of said at least one olefinic hydrocarbon reactant and said olefinic hydrocarbon compound has from 3 to 18 carbon atoms and is represented by the formula $R'_2C{=}CR'{-}CHR'_2$, wherein each R' is independently selected from the group consisting of hydrogen and hydrocarbyl radicals; and wherein each of said at least one olefinically unsaturated mononitrile reactant and said olefinically unsaturated mononitrile compound has from 3 to 18 carbon atoms and is represented by the formula $RCH{=}CR{-}CN$, wherein each R is independently selected from the group consisting of hydrogen and hydrocarbyl radicals;

wherein said at least one monoadduct reaction product comprises compounds having the structural formula

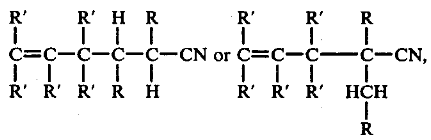

wherein R and R' are as defined above;

wherein said at least one olefinically unsaturated dinitrile product is formed by the monoaddition of a said olefinically unsaturated mononitrile reactant and said monoadduct reaction product;

wherein said reaction conditions comprise a temperature in the range of about 100° C. to about 500° C., a pressure in the range of about atmospheric to about 100,000 psig, and a liquid hourly space velocity in the range of about 0.05 to about 20;

wherein the mol ratio of said at least one olefinically unsaturated mononitrile reactant to said at least one olefinic hydrocarbon reactant is in the range of about 10:1 to about 0.1:1;

wherein at substantially any point in said plurality of tank reactors in series the concentration of said monoadduct reaction product in the resulting mixture is within the range of about 10 to about 90 weight percent of the total reaction mixture;

wherein the amount of said diluent is in the range of about 0.01 to about 1.25 parts by weight of total diluent per part by weight of said olefinically unsaturated mononitrile reactant if at least one of said plurality of tank reactors in series is operated downflow; and wherein the amount of said diluent is in the range of about 0.01 to about 40 parts by weight of total diluent per part by weight of said olefinically unsaturated mononitrile reactant if all of said plurality of tank reactors in series are operated upflow.

18. A process in accordance with claim 17 wherein said plurality of tank reactors in series comprises three tank reactors in series.

19. A process in accordance with claim 18 wherein said plurality of tank reactors is a stirred tank reactor.

20. A process in accordance with claim 17 wherein said at least one olefinic hydrocarbon reactant, said at least one olefinically unsaturated mononitrile reactant, said at least one monoadduct reaction product of an olefinic hydrocarbon and an olefincally unsaturated mononitrile compound, and said diluent are introduced into a lower zone of a first one of said plurality of tank reactors in series; any unreacted reactants and the reaction products from said first one of said plurality of tank reactors in series being removed from an upper zone of said first one of said plurality of tank reactors in series and being introduced into a lower zone of the second tank reactor in series; the process of introducing reactant and reaction products into a lower zone of each tank reactor in series and removing reactants and reaction products from an upper zone of each tank reactor in series continuing until said at least one olefinically unsaturated dinitrile product is removed from an upper zone of the last tank reactor in series.

21. A process in accordance with claim 17 wherein said diluent comprises at least 50 weight percent water; the balance, if any, of said diluent being nonreactive with the reactants and the reactant products.

22. A process in accordance with claim 17 wherein said at least one olefinically unsaturated mononitrile reactant is acrylonitrile, wherein said olefinically unsaturated mononitrile compound is acrylonitrile, wherein said at least one olefinic hydrocarbon reactant is isobutylene, and wherein said olefinic hydrocarbon compound is isobutylene.

23. A process in accordance with claim 22 further comprising recovering from the resulting reaction effluent said at least one olefinically unsaturated dinitrile reaction product.

24. A process in accordance with claim 17 wherein said at least one olefinically unsaturated mononitrile reactant is acrylonitrile, wherein said olefinically unsaturated mononitrile compound is acrylonitrile, wherein said at least one olefinic hydrocarbon reactant is isobutylene, and wherein said olefinic hydrocarbon compound is isobutylene.

* * * * *